US009259310B2

United States Patent
Schachar et al.

(10) Patent No.: US 9,259,310 B2
(45) Date of Patent: Feb. 16, 2016

(54) DEVICE AND METHOD FOR CILIARY MUSCLE COMPRESSION FOR INCREASING THE AMPLITUDE OF ACCOMMODATION

(71) Applicants: Ira H. Schachar, Ann Arbor, MI (US); Ronald A. Schachar, La Jolla, CA (US)

(72) Inventors: Ira H. Schachar, Ann Arbor, MI (US); Ronald A. Schachar, La Jolla, CA (US)

( * ) Notice: Subject to any disclaimer, the term of this patent is extended or adjusted under 35 U.S.C. 154(b) by 129 days.

(21) Appl. No.: 13/840,707

(22) Filed: Mar. 15, 2013

(65) Prior Publication Data

US 2014/0277051 A1    Sep. 18, 2014

(51) Int. Cl.
*A61F 2/14* (2006.01)
*A61F 2/16* (2006.01)
*A61F 9/007* (2006.01)
*A61F 9/00* (2006.01)

(52) U.S. Cl.
CPC .............. *A61F 2/1694* (2013.01); *A61F 2/14* (2013.01); *A61F 9/0017* (2013.01); *A61F 9/00781* (2013.01); *Y10T 156/10* (2015.01)

(58) Field of Classification Search
CPC ......... A61F 2/14; A61F 2/147; A61F 2/1694; A61F 2/15; A61F 9/0017; A61F 9/00781; B21B 1/16–1/20
See application file for complete search history.

(56) References Cited

U.S. PATENT DOCUMENTS

| | | |
|---|---|---|
| 2007/0293872 A1 | 12/2007 | Peyman |
| 2008/0228127 A1 | 9/2008 | Burns |
| 2010/0010416 A1 | 1/2010 | Juan, Jr. |
| 2012/0035524 A1 | 2/2012 | Silvestrini |
| 2012/0059461 A1 | 3/2012 | Badawi |

OTHER PUBLICATIONS

PCT ISR and WO Ser. No. PCT/US2014/019606 dated Jun. 27, 2014.

*Primary Examiner* — Howie Matthews
(74) *Attorney, Agent, or Firm* — Carlos R. Villamar; The Villamar Firm PLLC

(57) ABSTRACT

The present invention relates generally to a device and method for the treatment of, ocular hypertension, glaucoma, and increasing the amplitude of accommodation. In an illustrative embodiment, the device includes a self-expanding wire. Once the device is within the posterior chamber between the iris and anterior lens capsule, the wire expands to compress the ciliary muscle. When the device is in place the scleral spur is moved posteriorly resulting in traction on the trabecular meshwork, which causes a reduction in intraocular pressure for the treatment of patients with ocular hypertension and glaucoma. In addition, the compression of the ciliary muscle increases the force of contraction of the ciliary muscle, which increases the amplitude of accommodation in patients with deficient accommodative amplitude and presbyopia.

12 Claims, 3 Drawing Sheets

DEVICE AND METHOD FOR CILIARY MUSCLE COMPRESSION FOR INCREASING THE AMPLITUDE OF ACCOMMODATION

BACKGROUND OF THE INVENTION

1. Field of the Invention

The present invention relates generally to increasing the amplitude accommodation of the eye, and the like, and more particularity to a device and method for increasing the force and effectiveness of ciliary muscle contraction by compressing the ciliary muscle for the treatment of presbyopia, ocular hypertension, and glaucoma, and the like.

2. Discussion of the Background

The age-related reduction of amplitude of accommodation that results in the manifestation of presbyopia and the age-related increase in intraocular pressure that can lead to ocular hypertension occur universally and leads to the loss of the ability to read in the fifth decade of life and in some individuals to glaucoma, which can result in blindness. However, conventional methods and devices for treatment of such disorders are still yet to be improved. Accordingly, there is a need for a device and method for the treatment of presbyopia, ocular hypertension, glaucoma, and the like, which can increase the amplitude of accommodation and increase aqueous humor outflow by increasing the force of ciliary muscle contraction, and the like.

SUMMARY OF THE INVENTION

The present invention disclosed herein includes an apparatus and method to treat presbyopia, lower intraocular pressure and increase the amplitude of accommodation by controlled compression of the ciliary muscle. The device of the present invention involves using a small bore hypodermic needle or cannula, typically 25 gauge or smaller, to insert a uniquely shaped thin wire device into the posterior chamber of eye between the iris and anterior lens capsule that once within the posterior chamber expands to a predetermined size to ensure the magnitude of anterior ciliary muscle compression is precisely predictable. The device is designed to avoid compression of the cardinal anterior ciliary arteries. The compression of the ciliary muscle increases the force of ciliary muscle contraction and its baseline tension. This results in posterior movement of the scleral spur and more effective transduction of ciliary muscle force to the zonules of the lens, which increases trabecular meshwork aqueous humor outflow resulting in lower intraocular pressure and an increase in the amplitude of accommodation. Advantageously, these changes in the ciliary muscle offer a new method for treating ocular hypertension, glaucoma and presbyopia.

Accordingly, it is an aspect of the present invention to use a thin wire device that can self expand to a predictable size and shape within the posterior chamber between the iris and the anterior lens capsule.

It is a further aspect of the present invention to use a thin wire device that compresses the ciliary muscle in at least four quadrants.

It is a further aspect of the present invention for a thin wire device to have a unique shape to prevent compromised blood flow of the cardinal anterior ciliary blood vessels upon expansion.

It is a further aspect of the present invention to use a thin wire device of titanium and nickel.

It is a further aspect of the present invention to use a thin wire device of stainless steel that can be expanded to a predictable size within the posterior chamber between the iris and anterior lens capsule.

It is a further aspect of the present invention to use a uniquely designed thin tube to expand with a gel, air or water pressure in order to control the size of expansion of the tube within the posterior chamber between the iris and anterior lens capsule.

It is a further aspect of the present invention to use a thin plastic wire device that can self expand to a predictable size within the posterior chamber between the iris and anterior lens capsule.

It is a further aspect of the present invention to use a thin plastic wire device made of tightly woven polyester filaments.

It is a further aspect of the present invention to use a thin plastic wire device that does not biodegrade with time.

It is a further aspect of the present invention to use a thin plastic wire device that does biodegrade with time.

It is a further aspect of the present invention to place the wire device in the posterior chamber between the iris and anterior lens capsule using a small 25 gauge hypodermic needle.

It is a further aspect of the present invention that the collapsed wire device in its unexpanded state can have an outer width of approximately 200 microns and a length of approximately 14 mm.

It is a further aspect of the present invention that the wire device can expand radially to have an approximate maximum outer diameter of 14 mm in the oblique meridians; that is, the 45-degree meridians, and approximately 9 mm in the cardinal meridians, that is, the vertical and horizontal meridians.

It is a further aspect of the present invention for the wire device that it can apply sufficient pressure, within the range of capillary and systolic blood pressure, when in posterior chamber between the iris and anterior lens capsule to compress the ciliary muscle.

It is a further aspect of the present invention that the length of the wire device is approximately 14 mm in length when unexpanded.

It is a further aspect of the present invention that the diameter of the wire of the wire device is approximately 100 microns.

It is a further aspect of the present invention that the wire of the wire device is round.

It is a further aspect of the present invention that the wire of the wire device is polygonal in shape.

It is a further aspect of the present invention that the wire of the wire device is a flat ribbon.

It is a further aspect of the present invention that the wire of the wire device is square.

It is a further aspect of the present invention that the wire device is made of an expandable hydrogel.

It is a further aspect of the present invention that the needle used to insert the wire device can be retracted so that the wire device can be properly placed within the posterior chamber between the iris and anterior lens capsule.

It is a further aspect of the present invention that the wire device is made with a laser and configured to maximize final expansion and rigidity and form the required expanded shape, by making rectangular shaped holes, round shaped holes, elliptical shaped holes, and polygonal shaped holes.

It is a further aspect of the present invention that a total mass of material remaining in the expandable wire device is more or less than a mass removed by the laser in making the holes.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention below, it may be advantageous to set forth definitions of certain words and phrases used throughout this patent document: the terms "include" and "comprise" as well as derivatives thereof, mean inclusion without limitation; the term "or," is inclusive, meaning and/or; the phases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior uses, as well as future uses, of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts.

DETAILED DESCRIPTION OF THE INVENTION

Figure 1:
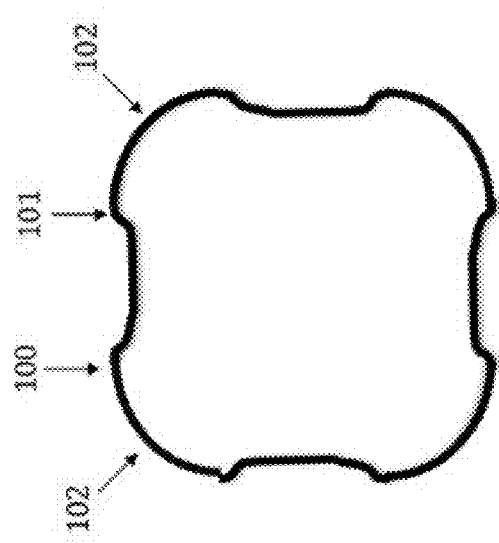
FIG. 1 illustrates a schematic diagram of an embodiment of a self-expanding wire device when fully expanded.

The present invention includes recognition that ocular hypertension and reduction of the amplitude of accommodation are common disorders that can lead to glaucoma and loss of the ability to read. However, conventional methods and devices for treatment of such disorders are still yet to be improved.

Ocular hypertension is defined as elevated pressure within the eye that is above normal. Various topical and systemic medications are commonly used to lower intraocular pressure. These medications may have disadvantages. They require repetitive use and consequently, compliance is difficult and costly. Additionally, these medications have unwanted side effects, which may even be life threatening.

An alternate method to medication employs a laser to lower the intraocular pressure in the eye by increasing aqueous outflow. Laser energy is directed through the cornea at the trabecular meshwork (the site of aqueous outflow) or to the immediately adjacent tissue area to produce holes, which increase the volume of outflow. Multiple treatments are usually required because the benefit from these holes declines with time. These frequent treatments can cause pigment dispersion within the eye, which can block aqueous outflow and lead to an increase in intraocular pressure.

A further alternative method for reducing intraocular pressure involves making a surgical connection between the anterior chamber of the eye and the subconjunctival space. These methods include trabeculectomy to remove part of the trabecular meshwork through a partial thickness scleral flap to permit drainage of aqueous humor through the scleral flap into the subconjunctival space, or making a channel from the inner trabecular meshwork to Schlemn's canal or placing a tube between the anterior chamber and the subconjunctival or sub-scleral space. All of these methods have disadvantages. The surgical connection between the anterior chamber and the subconjunctival space can be too large causing excessive aqueous humor drainage resulting in hypotony and phthisis bulbi. The connection between the anterior chamber and the subconjunctival/subscleral space and/or Schlemn's canal can close from fibrosis with a return of increased intraocular pressure. The connection between the anterior chamber and the subconjunctival space offers potential access to bacteria, which can result in endophthalmitis with consequential loss of the eye. Furthermore, all these surgical techniques require significant surgical skill and can be complicated and cause intra and extraocular hemorrhage. The surgery can result in conjunctival belbs that can disturb the tear film resulting in dry eye and the conjunctival belb can be cosmetically displeasing.

Alternatively, ultrasound or a laser is used to destroy the pigmented epithelium of the pars plicata of the ciliary body to lower intraocular pressure. This procedure reduces aqueous production by destroying the site responsible for the production of aqueous humor. These procedures usually require multiple applications and can cause significant pigment dispersion, iris atrophy, sympathetic ophthalmia (an autoimmune reaction against the untreated eye), hypotony, and phthisis bulbi. Clearly, there exists a need for a device that lowers intraocular pressure for extended periods of time with minimal side effects or heavy reliance on surgical skill.

Accommodation is the ability of the eye to focus at near. The young, emmetropic eye can focus on objects ranging from approximately 7 cm (the near point) to infinity in less than a second. This action is regulated by the ciliary muscle, which, upon its contraction, induces an alteration in the shape of the crystalline lens of the eye. Unfortunately, this action becomes less effective with age resulting in a progressive decline in accommodative amplitude (making the near point more remote). This progressive decline in accommodative amplitude occurs at a linear rate time so that by the mid-forties, the near point has receded beyond the normal working distance. When this occurs, the patient has developed what is known as presbyopia, which progressively worsens until the late fifties when virtually no accommodation remains.

There are a number of current treatments for presbyopia. The most common are reading aids, which utilize bifocal, trifocal or multifocal lenses. These can take the form of either spectacles or contact lenses. In both cases, there are significant disadvantages. Reading aids can only be used at a finite number of focal distances, are difficult to use, restrict the visual field, and can decrease contrast sensitivity. In addition, contact lenses are difficult to wear due to an age-related change in the tear film.

Surgical options have also been explored to deal with the onset of presbyopia. Laser assisted keratomeleusis (LASIK) has been used to make the cornea multifocal, or to insert an intracorneal lens or an artificial intracorneal pupil, or to set one eye for near vision and the other eye for distance vision. Unfortunately, these methods have disadvantages, including a decrease in contrast sensitivity, an increase in glare, the appearance of diffraction patterns, decreased night vision, and/or loss of stereopsis. Multifocal or accommodating intraocular lenses have been used to replace the normal crystalline lenses of patients, but carry similar disadvantages in addition to the potential complications of cataract surgery including retinal detachment and endophthalmitis.

A final surgical approach has been to expand the sclera to increase the effective working distance of the ciliary muscle to increase the accommodative amplitude. This has been achieved with both scleral incisions and implant surgery. These procedures have a number of disadvantages. Scleral incisions heal with time dramatically reducing their effect on accommodative amplitude. Implants can extrude with time or cause anterior-segment ischemia resulting in potential loss of the eye. Furthermore, the implants require significant surgical skill for proper placement, and even when placed correctly, changes in scleral elasticity can decrease their effect over time. Consequently, there is a need in the art for a device that can increase the amplitude of accommodation that is easy to place, is consistent with routine intraocular surgical techniques and can remain in place for an extended period time with minimal side effects.

FIGS. 1-4, which are used to describe the various embodiments and principles of the present invention are by way of illustration and should not be construed in any way to limit the scope of the invention. Those skilled in the art will understand that the principles of the present invention may be implemented in any type of wire device that can expand within the posterior chamber of the eye between the iris and the anterior lens capsule. Table 1, below, lists the element numbers of FIGS. 1-3 and a description thereof.

TABLE 1

Figure 2:
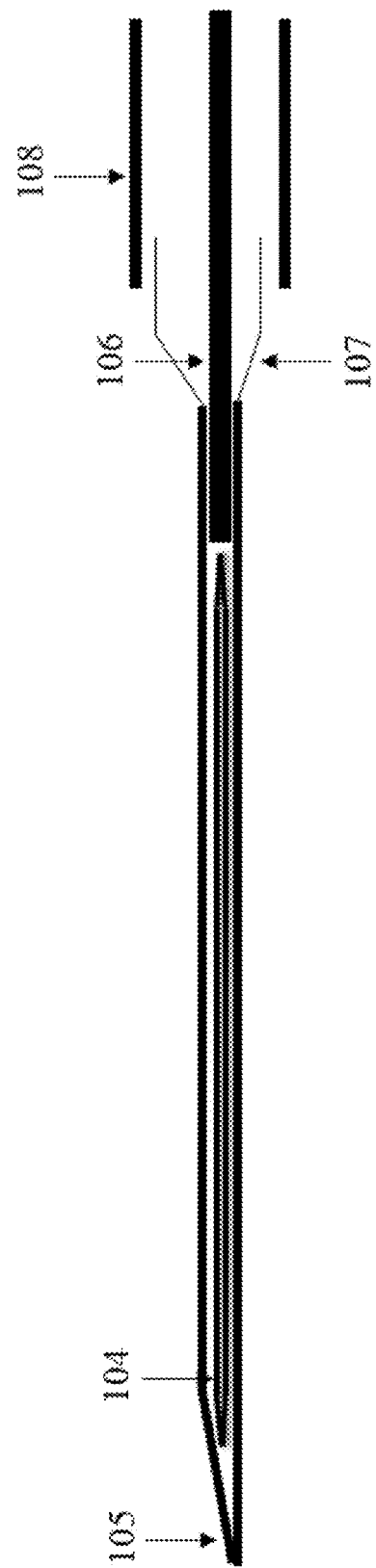
FIG. 2 illustrates a schematic diagram of an embodiment of a wire device before expansion while in a self retracting 25 gauge needle.
Figure 3:
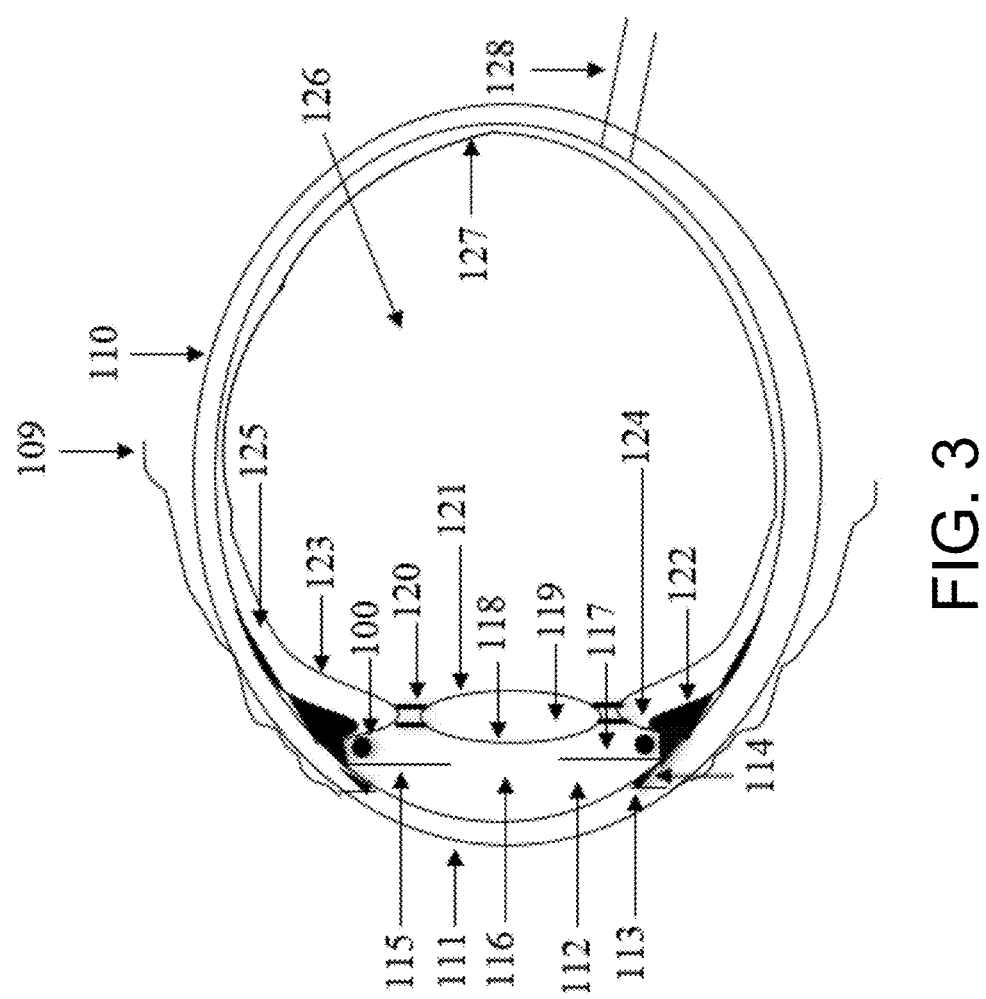
FIG. 3 illustrates a schematic diagram of an embodiment of a wire device placed within the posterior chamber of the eye between the iris and anterior lens capsule in accordance to the present invention.

List of Element Numbers for FIGS. 1-3

FIG. 1 - expanded wire device
100 - expanded wire device
101 - wire of the device
102 - the maximally expanded oblique meridian, 45 degrees, portions of the wire device
103 - the maximally expanded cardinal meridian, vertical and horizontal, portions of the wire device
FIG. 2 - unexpanded wire device within a retractable 23 gauge hypodermic needle
104 - unexpanded wire device
105 - 25 gauge hypodermic needle
106 - stop within hypodermic needle
107 - hub of hypodermic needle
108 - cylinder into which the hypodermic needle is retracted when the wire device is placed within the posterior chamber of the eye between the iris and anterior lens capsule
FIG. 3 -compression of the ciliary muscle when the expanded wire device is within the posterior chamber of the eye between the iris and anterior capsule
109 - conjunctiva
110 - sclera
111 - cornea
112 - anterior chamber
113 - trabecular meshwork
114 - scleral spur TABLE 1-continued List of Element Numbers for FIGS. 1-3

115 - iris
116 - pupil
117 - posterior chamber
118 - anterior lens capsule
119 - lens
120 - zonules
121 - posterior lens capsule
122 - ciliary muscle
123 - ciliary body
124 - pars plicata of the ciliary body
125 - pars plana
126 - vitreous
127 - retina
128 - optic nerve FIG. 1 illustrates a schematic diagram of a device for the treatment of ocular hypertension, glaucoma, and the like, and for increasing the amplitude of accommodation by compression of the ciliary muscle, and the like, and which employs a self-expanding wire device 100. The diameter of the wire 101 that comprises the wire device is approximately 100 microns. The maximally expanded oblique meridians, 45 degrees, portions of the wire device 102 apply pressure to the ciliary muscle while the maximally expanded cardinal meridians, vertical and horizontal portions of the wire device 103 do not apply pressure to the horizontal and vertical anterior ciliary blood vessels. In FIG. 1, welding or a laser or any other suitable device can be used to make the wire device to maximize final expansion, rigidity, and the like. The total mass of the material remaining in the final wire device can be more or less than the mass that was removed by the laser to make the wire device, and the like.

FIG. 2. illustrates a schematic diagram of device of FIG. 1, when the unexpanded wire device 104 is within a retractable 25 gauge hypodermic needle 105, which has a stop 106 near its proximal end, so that the needle 105 along with its hub 107 can be retracted into a cylinder 108 to facilitate precise placement of the wire device 104 within the posterior chamber of the eye between the iris and anterior lens capsule.

FIG. 3. illustrates the eye with the conjunctiva 109, sclera 110, cornea 111, anterior chamber 112, trabecular meshwork 113, scleral spur 114, iris 115, pupil 116, posterior chamber 117, anterior lens capsule 118, lens 119, zonules 120, posterior lens capsule 121, ciliary muscle 122, ciliary body 123, pars plicata of the ciliary body 124, pars plicata of the ciliary body 124, pars plana 125, vitreous 126, retina 127, optic nerve 128, and the expanded wire device 100 within the posterior chamber of the eye between the iris and anterior lens capsule compressing the ciliary muscle 122 and moving the scleral spur 114 posteriorly and opening the trabecular meshwork 113.

Thus, the present invention disclosed herein includes an apparatus and method to lower intraocular pressure and increase the amplitude of accommodation by controlled compression of the ciliary muscle.

The device of the present invention involves using a hypodermic needle or cannula with a small outer diameter having a range from 21 gauge to 30 gauge. In an illustrative embodiment, a 27 gauge hypodermic needle with an ultra thin wall is used to insert the wire device within the posterior chamber of the eye between the iris and anterior lens capsule. Once the wire device is within posterior chamber between the iris and anterior lens capsule it expands so that its oblique meridians have an outer diameter of approximately 14 mm and its cardinal meridians have an outer diameter of approximately 9 mm. In an illustrative embodiment, the horizontal diameter of the wire device expands approximately 45 times the diameter it is when in the hypodermic needle or cannula and the oblique meridians expand approximately 70 times the diameter it was when in the hypodermic needle or cannula.

The wire device is made of materials that can expand when mechanical compression, temperature, or hydration is changed, such as titanium and nickel or an expandable plastic or hydrogel, and the like. Alternatively, a chemical reactant can be applied to expand the wire device or the wire device can be a tube through which pressurized water or air can be placed to expand the wire device. Alternatively, the device could be made of stainless steel or other biocompatible metal or plastic such as nylon or polypropylene, or the like, in which bending energy is used to expand the wire device.

The original, unexpanded, width of the wire device, has a range of 0.010 mm to 0.30 mm. In an illustrative embodiment, the original diameter of the wire of the wire device is approximately 0.10 mm to facilitate insertion through an ultrathin walled 27 gauge hypodermic needle, and the like.

The magnitude of the ciliary muscle compression is dependent on the expansion and stiffness of the wire device. The wire device can have approximate circumferences from 25 mm to 100 mm depending on the size of the eye in which it will be inserted. In an illustrative embodiment, the wire device has an approximate circumference of 44 mm with a maximum expanded diameter of 14 mm.

To facilitate insertion of the wire device within posterior chamber of the eye between the iris and anterior lens capsule and to avoid damage and erosion of the ciliary body epithelium, ciliary body, ciliary muscle, iris, zonules and anterior lens capsule, the wire of the wire device is smooth.

The wire device may or may not initially expand when injected into the posterior chamber between the iris and anterior lens capsule. The wire device may slowly expand to compress the ciliary muscle. In an illustrative embodiment, the wire device may be folded when placed in the posterior chamber and may unfold slowly so that the fully expanded device is between the iris and anterior lens capsule and compresses the ciliary muscle. In an another illustrative embodiment, as the device is injected behind the iris and anterior to the anterior lens capsule, it expands against the ciliary body and then as the rest of the device is injected it is maintained between the injecting needle and the anterior lens capsule by the bottom of the injecting need to ensure the entire wire device expands behind the iris in the posterior chamber between the iris and anterior lens capsule. In another illustrative embodiment. The part of the wire device expands between the iris and the anterior lens capsule while the rest of the device expands anterior to the iris in the anterior chamber. Then using a forceps or small grasping instrument or specially designed hook, the part of the wire device in the anterior chamber is placed behind the iris so that the entire wire device is in the posterior chamber between the iris and anterior lens capsule. In another illustrative embodiment, a biodegradable or removal thin plate device may also be used to ensure the wire device expands behind the iris. The plate maybe attached to the insertion needle or maybe injected with the wire device. The plate device may expand once the needle is inserted in the eye to completely or partially cover the pupil and collapse to permit easy removal from the eye. In another illustrative embodiment, prior to injecting the wire device in the posterior chamber, a viscoelastic substance is injected into the anterior and posterior chamber to protect the corneal endothelium, anterior lens capsule, lens and the other structures of the eye. The viscoelastic substance may or may not be removed from the eye once the wire device is injected into the eye between the iris and the anterior lens capsule.

The expansion of the wire device determines the magnitude of the ciliary muscle compression. One size of the wire device may be used for all patients; however, the dimensions of the wire device required for a given patient, may be individualized by measuring the diameter of the ciliary muscle with optical coherence tomography or ultrasonography or magnetic resonance imaging.

The wire device is made from biocompatible materials widely accepted by those skilled in the art such as titanium and nickel, stainless steel, expandable plastics, and the like, which may or may not be biodegradable.

The wire device should be relatively stiff to obtain sufficient ciliary muscle compression. In addition to the material properties and circumference of the wire device, the thickness of the wire of the wire device will determine the magnitude and area of the ciliary muscle compression. The thickness of the wire of the wire device can be from 0.01 mm to 0.3 mm and be round, rectangular, polygonal or a combination of these shapes. The wire of the wire device may be made from solid material or multiple fibers, or multiple individual components such as epoxy resins, plastics, hydrogels, or silicates, or silicones or carbon materials.

The wire device can be made by welding a wire together or by using a laser to cut the device from a ribbon or plate. The wire device may be made by injection molding. In an illustrative embodiment, a laser maybe used to drill holes in the wire to obtain the desired material properties.

The wire device may or may not be coated or impregnated within its structure with a medication (e.g., pharmaceutical or biologic) or several medications that can slowly elude over time. The wire device may contain a muscle stimulant or growth factor to improve and enhance ciliary muscle contraction and function of he ciliary muscle.

The wire device may elude any of the following biological agents: antiproliferative agents, antineoplastic agents, antioxidants, endothelial cell growth factors, smooth muscle cell growth and/or migration inhibitors, thrombin inhibitors, immunosuppressive agents, anti-platelet aggregation agents, collagen synthesis inhibitors, therapeutic antibodies, nitric oxide donors, antisense oligonucleotides, wound healing agents, therapeutic gene transfer constructs, peptides, proteins, extracelluar matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha agonists, proliferator-activated receptor-beta agonists, proliferator-activated receptor-alpha/beta agonists, proliferator-activated receptor-delta agonists, NF.kappa.beta., proliferator-activated receptor-alpha-gamma agonists, nonsterodial antiinflammatory agents, angiotensin converting enzyme (ACE) inhibitors, free radical scavangers, inhibitors of the CX3CR1 receptor, small interfering RNAs, and anti-cancer chemotherapeutic agents, and/or have antiinflammatory, anti-infective, anti-angiogenic, ocular hypotensive, anti-carcinogenic, anti-growth, anti-immunologic, anti-cytokines, anti-lipid and/or a fluid reducing properties, and the like.

The wire device may elude any of the following pharmaceutical agents: antiinflammatory agents, anti-infective agents, anti-angiogenic agents, ocular hypotensive agents, anti-carcinogenic agents, anti-growth agents, anti-immunologic agents, anti-lipid agents, kallikrien inhibitors, fluid reducing agents, cyclosporin A, mycophenolic acid, mycophenolate mofetil acid, rapamycin, rapamycin derivatives, biolimus A9, CCI-779, RAD 001, AP23573, azathioprene, pimecrolimus, tacrolimus (FK506), tranilast, dexamethasone, corticosteroid, everolimus, retinoic acid, vitamin E, rosglitazone, simvastatins, fluvastatin, estrogen, 17.beta.-estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol, and the like.

The method of manufacture of the wire device determines the magnitude of the expansion and stiffness of the wire device to precisely predict the amount of ciliary muscle compression.

Figure 4:
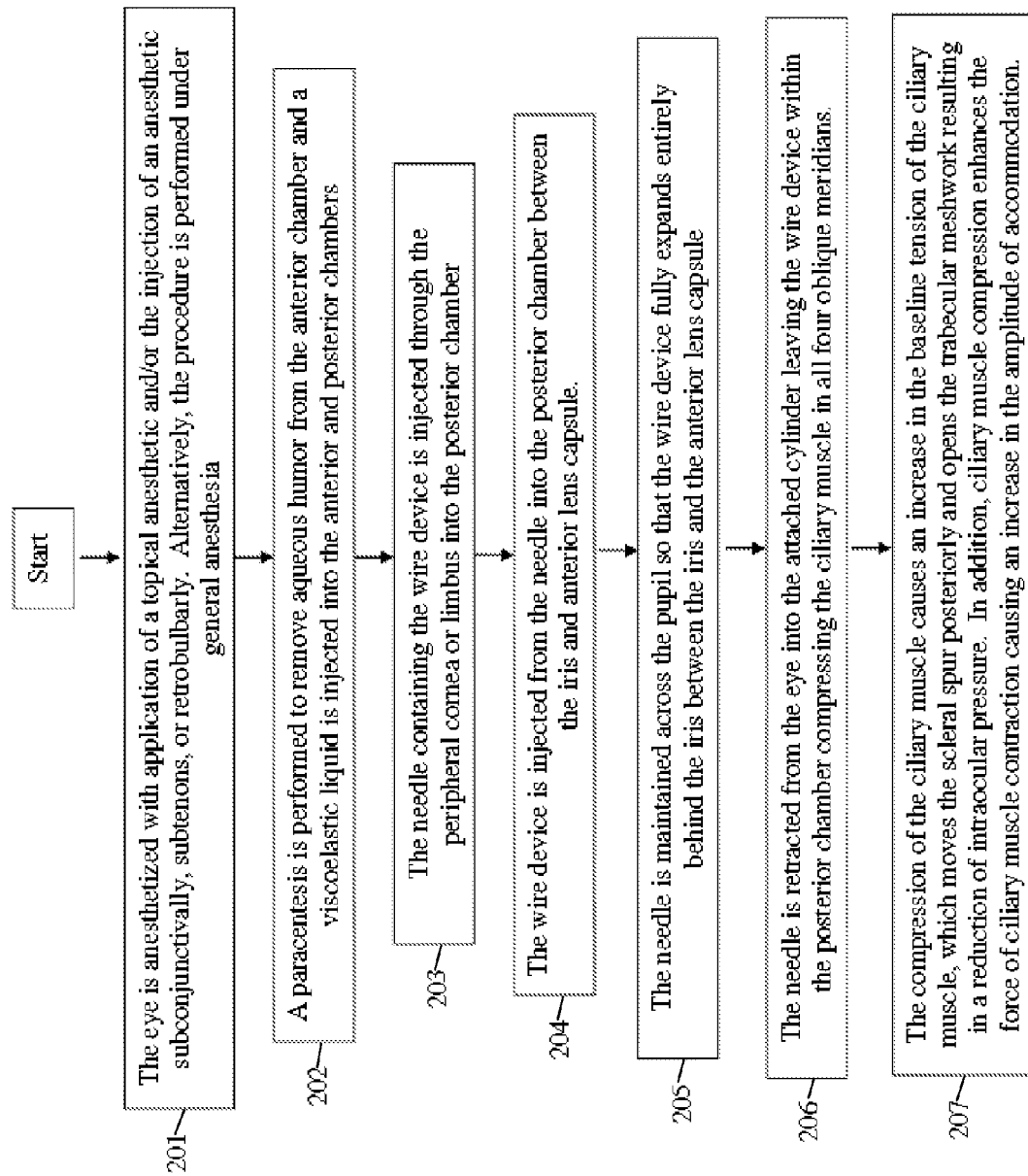
FIG. 4 is a flow diagram of an embodiment using a self-expanding wire device in accordance with the present invention.

FIG. 4 is a flow diagram of an embodiment using a self-expanding wire device in accordance with the present invention of FIGS. 1-3. In FIG. 4, at step 201, the eye is anesthetized with application of a topical anesthetic and/or the injection of an anesthetic subconjunctivally, subtenons, or retrobulbarly, and the like. Alternatively, the procedure is performed under general anesthesia. At step 202, a paracentesis is performed to remove aqueous from the anterior chamber and a viscoelastic liquid is injected into the anterior and posterior chambers. At step 203, the needle containing the wire device is injected through the peripheral cornea or limbus into the posterior chamber. At step 204, the wire device is injected from the needle into the posterior chamber between the iris and the anterior lens capsule. At step 205, the needle is maintained across the pupil so that the wire device fully expands entirely behind the iris between the iris and the anterior lens capsule. At step 206, the needle is retracted from the eye into the attached cylinder leaving the wire device within the posterior chamber compressing the ciliary muscle in all four oblique meridians. At step 207, the compression of the ciliary muscle causes an increase in the baseline tension of the ciliary muscle, which moves the scleral spur posteriorly and opens the trabecular meshwork resulting in a reduction of intraocular pressure. In addition, ciliary muscle compression enhances the force of ciliary muscle contraction causing an increase in the amplitude of accommodation. A miotic may be placed in the eye or applied topically to constrict the pupil, completing the procedure.

While the present invention has been described in connection with a number of illustrative embodiments and implementations, the present invention is not so limited, but rather covers various modifications and equivalent arrangements, which fall within the purview of the appended claims.

What is claimed is:

1. A device for effecting compression of a ciliary muscle of an eye, the device comprising:

a wire;

wherein the wire in a compressed state is configured to fit into a hypodermic needle or cannula for injection into a posterior chamber between an iris and an anterior lens capsule;

wherein the wire after injection is configured to self expand to a predetermined annular shape having four oblique median portions and four cardinal meridian portions; and wherein the wire self expands circumferentially, with the circumferential expansion greater in the four oblique meridian portions than in the four cardinal meridians portions, such that the device is configured to compress the ciliary muscle in four quadrants corresponding to the four oblique meridians, and prevent compromised blood flow of cardinal anterior ciliary blood vessels.

2. The device of claim 1, wherein the wire is made of biocompatible titanium and nickel, stainless steel or an expandable plastic or hydrogel or woven polyester filaments that is or is not biodegradable.

3. The device of claim 1, wherein the device is made from solid material or multiple fibers, or multiple components including epoxy resins, plastics, hydrogels, or silicates, or silicones or carbon materials.

4. The device of claim 1, wherein the wire has a thickness from 0.01 mm to 0.3 mm.

5. The device in claim 1, wherein the device when unexpanded fits into the hypodermic needle or the cannula of 20 gauge to 30 gauge.

6. The device of claim 1, wherein the device when unexpanded has a width in a range from 0.010 mm to 0.30 mm.

7. The device of claim 1, wherein the device when expanded has a maximum diameter ranging from 8 mm to 25 mm.

8. The device of claim 1, wherein the device when expanded has a circumference ranging from 25 mm to 100 mm.

9. The device in claim 1, wherein the device when expanded is configured to apply pressure to a ciliary muscle within a range of capillary and systolic blood pressure.

10. The device in claim 1, wherein the wire is round, rectangular, hexagonal, polygonal or a combination thereof.

11. The device in claim 1, wherein the device comprises a welded wire.

12. The device in claim 1, wherein the device comprises an injection molded wire.

* * * * *